(12) United States Patent
Durand et al.

(10) Patent No.: US 11,021,496 B2
(45) Date of Patent: Jun. 1, 2021

(54) MESOPOROUS ORGANOSILICA NANOPARTICLES, PRODUCTION METHOD THEREOF AND USES OF SAME

(71) Applicants: Centre national de la recherche scientifique, Paris (FR); Université de Montpellier, Montpellier (FR); NANOMEDSYN, Montpellier (FR)

(72) Inventors: Jean Olivier Durand, Palavas les Flots (FR); Jimenez Chiara Mauriello, Montpellier (FR); Sebastien Richeter, Montpellier (FR); Laurence Raehm, Montpellier (FR); Magali Gary-Bobo, Castelnau le Lez (FR); Marcel Garcia, Prades-le-Lez (FR); Marie Maynadier, Ceyras (FR)

(73) Assignees: CENTRE NATIONAL DE LA RECHERCHE SCIENTIFIQUE, Paris (FR); UNIVERSITÉ DE MONTPELLIER, Montpellier (FR); NANOMEDSYN, Montpellier (FR)

( * ) Notice: Subject to any disclaimer, the term of this patent is extended or adjusted under 35 U.S.C. 154(b) by 196 days.

(21) Appl. No.: 16/071,063

(22) PCT Filed: Jan. 18, 2017

(86) PCT No.: PCT/EP2017/050946
§ 371 (c)(1),
(2) Date: Jul. 18, 2018

(87) PCT Pub. No.: WO2017/125413
PCT Pub. Date: Jul. 27, 2017

(65) Prior Publication Data
US 2020/0140466 A1 May 7, 2020

(30) Foreign Application Priority Data
Jan. 19, 2016 (FR) ..................... 1650396

(51) Int. Cl.
| | |
|---|---|
| *C07F 7/18* | (2006.01) |
| *A61K 49/00* | (2006.01) |
| *B82Y 5/00* | (2011.01) |
| *B82Y 30/00* | (2011.01) |
| *B82Y 40/00* | (2011.01) |

(52) U.S. Cl.
CPC ........ *C07F 7/1804* (2013.01); *A61K 49/0036* (2013.01); *A61K 49/0093* (2013.01); *B82Y 5/00* (2013.01); *B82Y 30/00* (2013.01); *B82Y 40/00* (2013.01)

(58) Field of Classification Search
CPC .............. C07F 7/1804; A61K 49/0036; A61K 49/0096; A61K 41/0057; A61K 9/5123; A61K 47/6923; B82Y 5/00; B82Y 30/00; B82Y 40/00; A61P 35/00
See application file for complete search history.

(56) References Cited

U.S. PATENT DOCUMENTS

2013/0066098 A1* 3/2013 Rogers ................ A61K 47/548
558/160

FOREIGN PATENT DOCUMENTS

| FR | 2 935 974 A1 | 3/2010 |
| FR | 2 988 721 A1 | 10/2013 |
| WO | WO 2014/000180 A1 | 1/2014 |

OTHER PUBLICATIONS

Iamamoto et al., An. Acad. Bras. Ci., 2000 72, 1. (Year: 2000).*
Chen, et al. 2014 "Hollow mesoporous organosilica nanoparticles: A generic intelligent framework-hybridization approach for biomedicine" *Journal of the American Chemical Society* 136: 16326-16334.
Gary-Bobo, et al. 2012 "Cancer therapy improvement with mesoporous silica nanoparticles combining targeting, drug delivery and PDT" *International Journal of Pharmaceutics* 423: 509-515.
Hayashi, et al. 2014 "Photostable iodinated silica/porphyrin hybrid nanoparticles with heavy-atom effect for wide-field photodynamic/ photothermal therapy using single light source" *Adv. Funct. Mater.* 24: 503-513.
Hocine, et al. 2010 "Silicalites and mesoporous silica nanoparticles for photodynamic therapy" *International Journal of Pharmaceutics* 402: 221-230.
Mauriello-Jimenez, et al. 2015 "Porphyrin-functionalized mesoporous organosilica nanoparticles for two-photon imaging of cancer cells and drug delivery" *Journal of Materials Chemistry B* 3: 3681-3684.

* cited by examiner

*Primary Examiner* — Michael G. Hartley
*Assistant Examiner* — Leah H Schlientz
(74) *Attorney, Agent, or Firm* — Knobbe, Martens, Olson & Bear, LLP

(57) ABSTRACT

The present invention relates to mesoporous organosilica nanoparticles, the method of preparation thereof, and uses of the same in treatment by means of photodynamic therapy or in imaging.

17 Claims, 9 Drawing Sheets

Concentration of CM238 + Gemcitabine Nanoparticles (µg.mL⁻¹)

MESOPOROUS ORGANOSILICA NANOPARTICLES, PRODUCTION METHOD THEREOF AND USES OF SAME

FIELD

The present invention relates to mesoporous organosilica nanoparticles, the method of preparation thereof and uses of the same in treatment by means of photodynamic therapy or in imaging.

BACKGROUND

Photodynamic therapy is a non-invasive and selective therapeutic method that makes it possible to destroy cancerous or infected cells by using a photosensitising agent that is able to be activated by a light source of appropriate wavelength, in the visible or near infra-red spectral range. By the combined action of a photosensitising agent and light, molecular oxygen in the natural triplet state ($^3O_2$) is converted into singlet oxygen ($^1O_2$) that is highly cytotoxic and into other reactive oxidising species ($O^{2-}$, OH.). Singlet oxygen $^1O_2$ is a powerful oxidant that reacts with a number of cellular constituents such as saturated triacyl glycerols, membrane cholesterol, phospholipids, amino acids (histidine, tryptophan, methionine) and nucleic acids. Consequently singlet oxygen can thus lead to the destruction of cancer cells that are in contact with it, but is also toxic to the cells that surround it. In the absence of exposure to the appropriate light source, the photosensitising agent is not toxic to the cells, which thereby makes it possible to reduce any adverse side effects when compared to chemotherapy or radiation therapy.

The majority of photosensitising agents known in the prior art are excited by absorption of one photon. In this mode of excitation, the photosensitising agent is activated all along the path of the laser beam. Since the radiation cannot be specifically localised to the cells to be treated, the risk of damaging the tissues that are superposed over or adjacent to the tissues to be treated is one of the disadvantages of photodynamic therapy via the excitation of one photon.

Moreover, a majority of the photosensitising agents developed to date absorb a light in the visible spectral domain which can penetrate the skin only to a depth of a few millimetres, which considerably limits the scope and area of application of the photodymanic therapy.

Two-photon excited photodynamic therapy has developed in recent years and serves the purpose of overcoming these technical disadvantages.

In the two-photon excited mode, a photosensitising agent is excited simultaneously by the absorption of two photons so as to pass from its electronic state of rest into an excited state. In this mode of excitation, the said agent is activated only in the focus of the laser beams. Thus the radiation can consequently be localised more precisely to the tissues to be treated. In addition, this mode of excitation is obtained by means of a near infra-red light, which is able to penetrate deeper into the tissues.

The excitation by two photons may be obtained by an indirect approach by making use of the FRET method (transfer of energy between fluorescent molecules or Förster-type resonance energy transfer), or a direct approach by using a photosensitising agent that is capable of absorbing two photons.

Most of the two-photon absorbing photosensitising agents used to date are organic molecules. The use of these photosensitising organic molecules is however subject to the following limitations: these molecules are hydrophobic and require a delivery system, notably a particular formulation, in particular in the form of nanoparticles, for clinical application. These molecules do not efficiently target tumour cells and have a significant residence time in healthy tissues. Given that the majority of these molecules are activated by visible light, this results in adverse side effects causing destruction of healthy cells and these molecules can therefore not be used for the treatment of deeper tissues.

The international patent application WO 2013/144154 describes porous silica nanoparticles onto which porphyrin derivatives are grafted. However, these nanoparticles obtained after grafting are not sensitive enough to two-photon excitation so as to effective for an application in two-photon excited photodynamic therapy.

Another promising approach developed in recent years consists in embedding the photosensitising agents within silica nanoparticles, in particular mesoporous organosilica nanoparticles.

Periodic Mesoporous Organosilica Nanoparticles (PMO) belong to a new class of mesoporous materials and are of ever-increasing interest for their applications in the adsorption of molecules or gases, catalysis, immobilisation of enzymes, and in particular, drug delivery, on account of their biocompatibility, low hemolytic activity and very highly specific surface area. These PMO nanoparticles are prepared from alkoxysilanes which are connected by organic groups that can confer different chemical properties to the nanoparticles.

Mauriello-Jimenez et al. have described a type of mesoporous organosilica nanoparticles comprising a Zn-metallised porphyrin derivative having eight triethoxysilyl groups (*Journal of Mater Chem B*, 2015, 3, 3681-3684). These nanoparticles are capable of emitting fluorescence (fluorescing) after two-photon excitation and can therefore be applied in two-photon fluorescence imaging. However, they cannot be used in photodynamic therapy because of a lack of ability to generate singlet oxygen after two-photon excitation in order to destroy cancer cells.

Hayashi et al (*Adv Funct Mater* 2014, 24, 503-513) describe hybrid nanoparticles formed by porphyrin derivatives and iodised silicas. However, given that the method of preparation described in this document does not use a surfactant that allows for inducing porosity, the nanoparticles obtained are not porous.

WO 2014/000180 discloses mesoporous silica structures obtained by the reaction between a silane coupling agent and a porphyrin derivative. Given that the precursor used in this document is tetraethoxysilane or tetramethyloxysilane, the nanoparticles obtained are mesoporous silica nanoparticles (MSN), but are not mesoporous organosilica nanoparticles (PMO).

Chen et al (*Journal Am Chem Soc* 2014, 136, 10326-16334) disclose mesoporous organosilica nanoparticles forming a molecular cage that makes it possible to encapsulate doxorubicin. These nanoparticles are not photosensitive and can thus not be used as photosensitising agents in photodynamic therapy.

There is therefore still a need to develop new photosensitising agents that may be used in photodynamic therapy, which are in particular capable of being excited by two photons.

SUMMARY

In an entirely unexpected fashion, the inventors of the present invention have found a new class of mesoporous organosilica nanoparticles containing porphyrin derivatives, the said nanoparticles presenting a significant increase in the effective two-photon absorption cross section, and therefore being capable of generating singlet oxygen after irradiation with a near-infrared light, this providing the ability to destroy the cancer cells.

The object of the first aspect of the present invention is to provide novel mesoporous organosilica nanoparticles containing porphyrin derivatives.

Another object of the invention relates to pharmaceutical compositions comprising the said mesoporous organosilica nanoparticles, in particular pharmaceutical compositions for use thereof in the treatment of cancers, in particular by means of one-photon- or by two-photon excited photodynamic therapy.

Another object of the invention relates to the use of the said nanoparticles as photosensitising agents.

The invention also relates to the use of the said nanoparticles in one-photon or two-photon fluorescence imaging.

The object of the invention also relates to a nanoparticle preparation method for preparing the said nanoparticles, as well as the nanoparticles obtained by this method.

The present invention also provides a detection kit for detecting a pathology, such as a cancer, a tumour, or a cell proliferative disorder or disease.

The mesoporous organosilica nanoparticles of the present invention are formed by elements comprising or consisting of:

(i) a porphyrin derivative selected from among:
a compound having the formula A in which:

Either $R_1$, $R_2$, $R_3$, and $R_4$ all correspond to

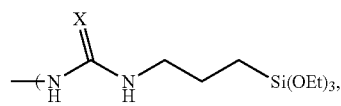

where X is the oxygen atom or the sulfur atom;

Or $R_1$, $R_2$, $R_3$, and $R_4$ all correspond to

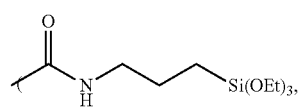

a compound having the formula B, C or D, in which Z is selected from the oxygen atom or the sulfur atom (B)

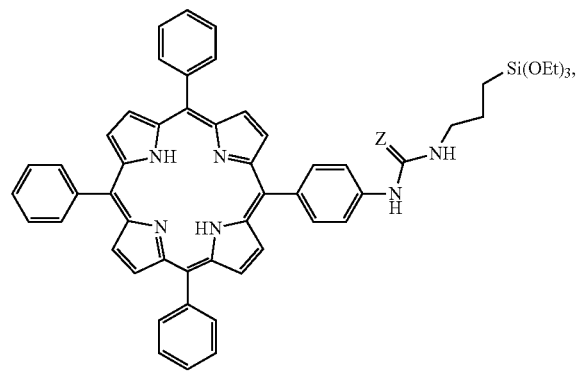

(C)

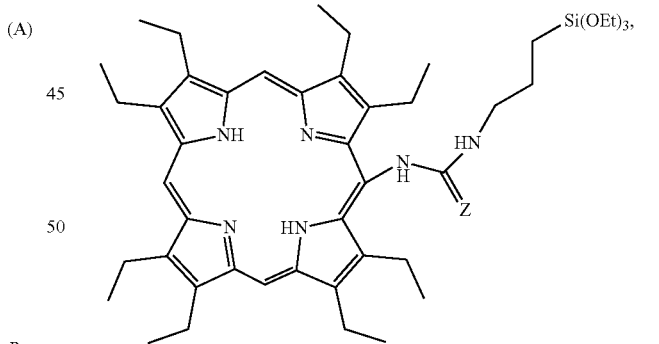

(D)

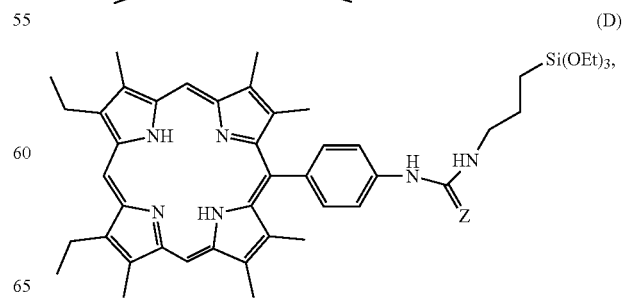

(A)

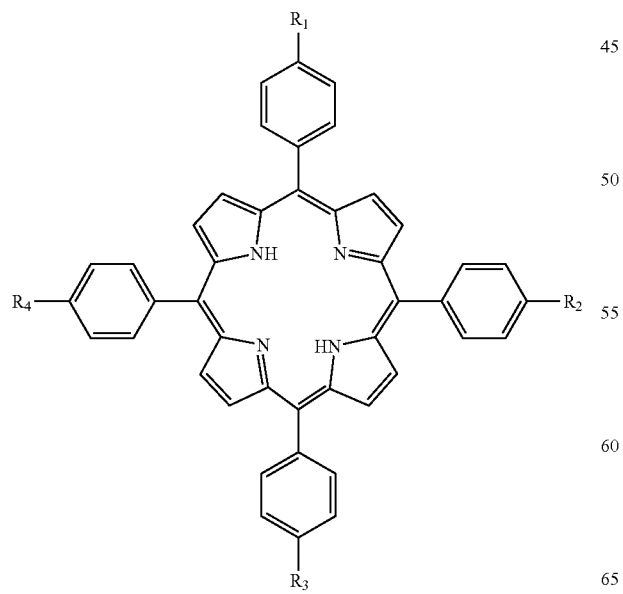

or
a compound E, F or G

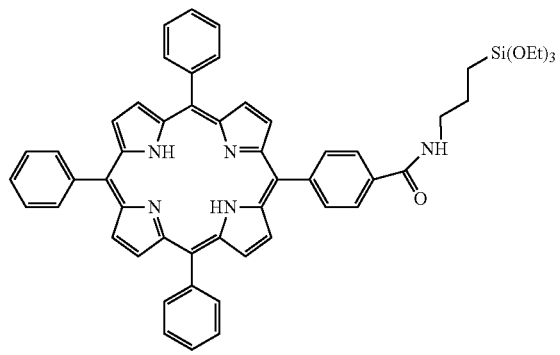

(E)

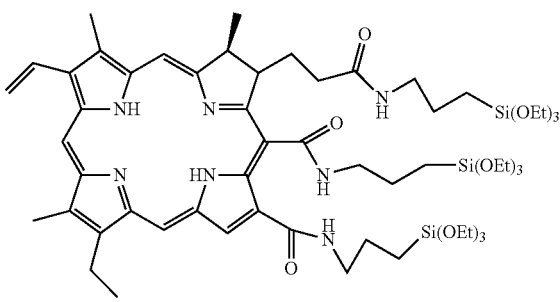

(F)

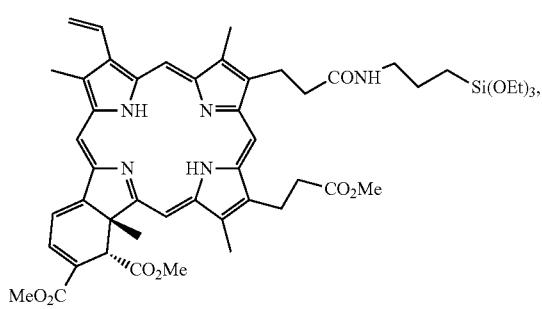

(G)

and
(ii) a compound having the formula I:

in which n represents an integer selected from 1 to 10, and possibly
(iii) a compound having the formula II

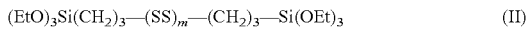

in which m is an integer that is equal to 2 or 4,
the said nanoparticles possibly encapsulating at least one hydrophilic and/or hydrophobic anticancer compound.

The term "mesoporous organosilica nanoparticles" is used to refer to a class of porous nanoparticles obtained from the organo triethoxysilane precursor, whose pore size is generally from 2 to 50 nm, in which the organic groups are embedded in a covalent manner into the matrix of the particles and form the structure of the particles.

The nanoparticles of the present invention covalently incorporate tetrasilylated porphyrins into the matrix and have pores with pore sizes of 2 to 10 nm, in particular of about 3 nm.

A porphyrin derivative, a compound having the formula I and possibly a compound having the formula II as defined here above are the structural elements that make it possible to form the matrix of basic mesoporous organosilica nanoparticles by a co-condensation under appropriate conditions.

The basic nanoparticles are photosensitising, and can be activated in particular by a one- or two photon light source, in particular by radiation having a wavelength of 400-1000 nm, in particular radiation having a wavelength of about 800 nm, and capable of generating singlet oxygen.

In bi-photonics, the excitation may be obtained by radiation having a wavelength of 750 to 1000 nm, in particular of 800 nm, and is preferably effected by way of three to twelve scans of 1.57 s each at a power measuring from 20 to 140 mW, advantageously from 50 to 100 mW, and better still around 80 mW and for a scanned surface of 1.5×1.5 mm$^2$, that is, a fluence of 10.6 J/cm$^2$ to 42.4 J/cm$^2$ by multiphoton microscopy. In single photonics, the irradiation may be obtained at a wavelength of 400 to 700 nm, in particular at 405 nm, and is preferably effected by irradiation for a period of 10 minutes at a power measuring 10 mW/0.32 cm$^{2'}$ that is a fluence of 18.75 J/cm$^2$.

In the context of the present invention, the terms "excitation", "activation" and "irradiation" are interchangeable when they relate to the absorption of one or two photons by the nanoparticles of the invention.

The terms "bi-photonic" and "(with) two-photon" may be used interchangeably with each other.

The terms "mono-photonic" and "(with) one-photon" are also interchangeable.

The diameter of the mesoporous organosilica nanoparticles described in the present invention may be from 20 to 400 nm, advantageously from 50 to 300 nm, more advantageously from 200 to 250 nm. These nanoparticles have a very high specific surface area, which may be from 100 to 1500 m$^2$/g, advantageously from 800 to 1000 m$^2$/g. This confers to the nanoparticles of the invention a very high efficacy for absorbing small-sized molecules. Thanks to this property, the nanoparticles of the invention are able to effectively encapsulate at least one type of chemical molecule having a molecular weight of less than 1000 Dalton, in particular a small-sized molecule of a medicament, such as a hydrophilic and/or hydrophobic anticancer compound.

According to the invention, the hydrophilic anticancer compound may be selected from gemcitabine, gemcitabine monophosphate, 5-fluorouracil, cytarabine, topotecane, irinotecane, or oxalylplatin; the hydrophobic anti-cancer compound may be selected from doxorubicin, paclitaxel, or camptothecin.

In contrast to the mesoporous silica nanoparticles known in the prior art, which are not able to effectively encapsulate a hydrophilic compound, such as gemcitabine or gemcitabine monophosphate, the basic nanoparticles of the invention, thanks to the hydrophobic environment within their pores, are particularly effective and advantageous for encapsulating the hydrophilic anticancer compounds, in particular for encapsulating gemcitabine or gemcitabine monophosphate.

The mesoporous organosilica nanoparticles of the present invention in which the porphyrin derivatives having the formula A are embedded are photosensitive to two-photon or one-photon excitation and is able to generate singlet oxygen after excitation, which allows for this type of nanoparticles to be used in photodynamic therapy, including two-photon excited photodynamic therapy.

In one embodiment, the nanoparticles of the present invention are formed by the elements comprising a porphyrin derivative corresponding to the formula A1:

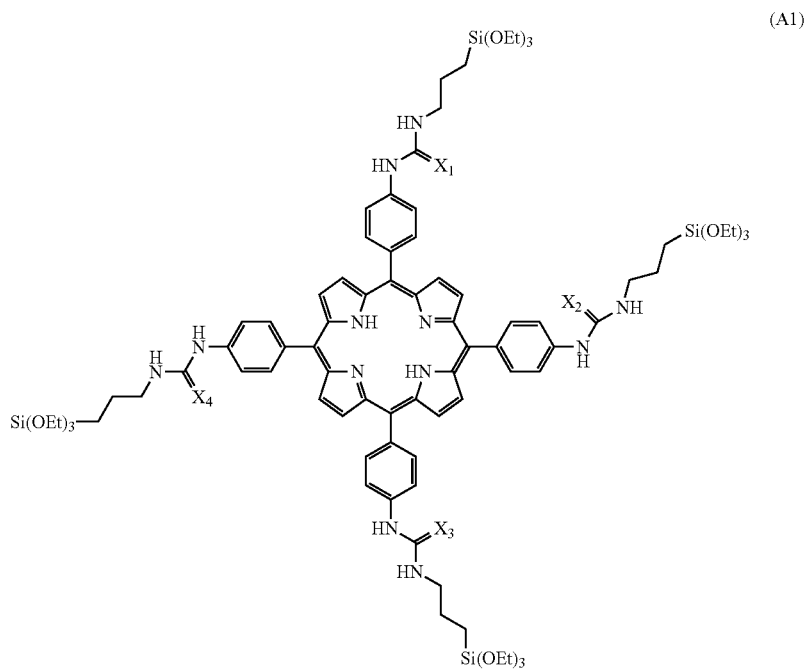

The basic nanoparticles of the invention are also capable of encapsulating several types of molecules, for example a hydrophilic compound and a hydrophobic compound.

In one particular embodiment, the mesoporous organosilica nanoparticles of the invention are formed by a porphyrin derivative having the formula A as defined here above. The said porphyrins aggregate into a J aggregate with a shift of the UV-Visible spectrum towards red (red-shifted). This confers to the nanoparticles the bi-photonic property with a fairly significant increase in the effective two-photon absorption cross section and may be excited by light having a wavelength of 750 nm to 800 nm.

The term "bi-photonic/two-photon property" is used to refer to the ability of the nanoparticles to simultaneously absorb two photons.

The term "J aggregate" is used to refer to a type of dye having an absorption band that is shifted to a higher wavelength with a greater absorption coefficient when it aggregates as a result of supramolecular self-organisation under the influence of a solvent or additive.

in which $X_1$, $X_2$, $X_3$, and $X_4$ are selected independently of each other from the oxygen atom or the sulfur atom.

One embodiment of the invention relates to the mesoporous organosilica nanoparticles formed by the elements constituted of:

(i) a porphyrin derivative as defined here above, and (ii) a compound having the formula I as defined here above.

In the context of the present invention, a compound having the formula I may be in particular bis(triethoxysilyl)methane, bis(triethoxysilyl)ethane, 1,3-bis(triethoxysilyl)propane, 1,4-bis(triethoxysilyl)butane, or 1,5-bis(triethoxysilyl)pentane.

The porphyrin derivative and the compound having the formula I as defined here above may be present in the nanoparticles of the invention with a molar ratio of between 2:98 and 20:80, in particular 10:90.

In one particular embodiment in, the nanoparticles are formed by the elements constituted of:

(i) a porphyrin derivative having the formula A, in particular a derivative having the

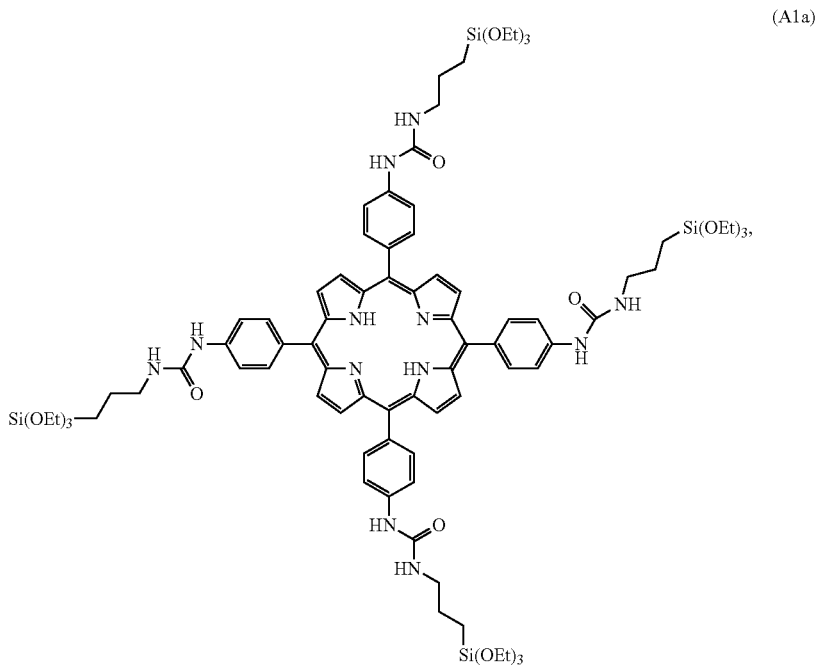

(A1a)

and (ii) a compound having the formula I as defined here above.

These nanoparticles are capable of being excited by two photons in the infra-red domain and of generating singlet oxygen.

In accordance with the invention, the terms "in the infra-red domain" and "near infrared", are understood to refer to the wavelength of a light source of between 700 and 1000 nm.

A more particular embodiment of the invention relates to the nanoparticles, hereinafter referred to as "NPs CM238", formed by the elements constituted of:
(i) a porphyrin derivative having the formula A1a, and
(ii) bis(triethoxysilyl)ethane.

In another particular embodiment, the nanoparticles are formed by the elements constituted of:
(i) a porphyrin derivative having the formula B, and
(ii) a compound having the formula I as defined here above.

Another more particular embodiment of the invention relates to the nanoparticles, hereinafter referred to as "NPs PMOS1", formed by the elements constituted of:
(i) a porphyrin derivative having the formula B, and
(ii) bis(triethoxysilyl)ethane.

One embodiment of the invention relates to the basic mesoporous organosilica nanoparticles formed by the elements constituted of:
(i) a porphyrin derivative as defined here above,
(ii) a compound having the formula I as defined here above, and
(iii) a compound having the formula II as defined here above.

Thanks to the presence of a compound having the formula II, this type of basic nanoparticles is biodegradable within a period of 48 hours by degrading into compounds that are eliminated by renal clearance with no toxicity.

According to the invention, a compound having the formula II is in particular bis triethoxysilylpropyl disulfide.

Within the matrix of this type of nanoparticles of the invention, the molar proportion between a porphyrin derivative, a compound having the formula I, and a compound having the formula II may be from 1 to 30%, from 10 to 90%, and from 10 to 90% respectively.

Advantageously, in the nanoparticles constituted by a porphyrin derivative, a compound having the formula I and a compound having the formula II, the molar proportion is, respectively, from 1 to 30% for the porphyrin derivative, from 40% to 90% for the compound having the formula I, less than 50% for the compound having the formula II.

In one particular embodiment, the nanoparticles are formed by the elements constituted of:
(i) a porphyrin derivative having the formula A, in particular a derivative having the formula A1a as defined here above,
(ii) a compound having the formula I as defined here above,
(iii) a compound having the formula II as defined here above.

These nanoparticles are both biodegradable and capable of being excited by two photons in the infra-red domain.

A more particular embodiment of the invention relates to the nanoparticles, hereinafter referred to as "NPs CM240", formed by the elements constituted of:
(i) a porphyrin derivative having the formula A1a,
(ii) bis(triethoxysilyl)ethane,
(iii) bis-triethoxysilylpropyl disulphide.

More particularly, the invention relates to nanoparticles, hereinafter referred to as "NP CM240-b", formed by the elements constituted of:
(i) a porphyrin derivative having the formula A1a, the molar proportion of which is from 1 to 10%,
(ii) bis(triethoxysilyl)ethane, the molar proportion of which is from 40 to 90%;

(iii) bis triethoxysilylpropyl disulphide, the molar proportion of which is less than 50%.

Another embodiment of the invention relates to mesoporous organosilica nanoparticles whose matrix is formed by a porphyrin derivative as defined here above, a compound having the formula I as defined here above, and possibly a compound having the formula II as defined here above, encapsulating at least one hydrophilic and/or hydrophobic anticancer compound, in particular a hydrophilic anticancer compound.

This type of nanoparticles shows an anticancer activity both by the production of singlet oxygen after the excitation of the nanoparticles by a near infra-red light source and the activity of the anti-cancer compound absorbed within the nanoparticles and shows a synergistic effect relative to the addition of the anticancer activity obtained by the said anticancer compound alone and that obtained by the photodynamic therapy alone.

When a hydrophilic or hydrophobic anticancer compound is present in the nanoparticles of the invention, the load of hydrophilic or hydrophobic anticancer compound as defined here above is from 2% to 100% by weight, in particular 40% by weight, relative to the initial weight of the nanoparticles prior to the encapsulation of the said anticancer compound.

In one particular embodiment, the nanoparticles are formed by the elements constituted of:
(i) a porphyrin derivative as defined here above,
(ii) a compound having the formula I as defined here above,
the said nanoparticles encapsulating at least one hydrophilic and/or hydrophobic anticancer compound.

In one particular embodiment of the invention, the nanoparticles are formed by the elements constituted of:
(i) a porphyrin derivative having the formula A, in particular a derivative having the formula A1a described here above,
(ii) a compound having the formula I as defined here above,
the said nanoparticles encapsulating gemcitabine or gemcitabine monophosphate.

A more particular embodiment of the invention relates to nanoparticles, hereinafter referred to as "NPs CM238+ gemcitabine", formed by the elements constituted of:
(i) a porphyrin derivative having the formula A1a,
(ii) bis(triethoxysilyl)ethane,
the said nanoparticles encapsulating gemcitabine.

Another embodiment of the invention relates to the nanoparticles formed by the elements constituted of:
(i) a porphyrin derivative as defined here above,
(ii) a compound having the formula I as defined here above,
(iii) a compound having the formula II as defined here above,
the said nanoparticles encapsulating at least one hydrophilic and/or hydrophobic anticancer compound.

This type of nanoparticles are biodegradable and show a synergistic anticancer activity relative to the addition of the anticancer activity obtained by the said anticancer compound alone and that obtained by photodynamic therapy alone.

In one particular embodiment of the invention, the nanoparticles are formed by the elements constituted of:
(i) a porphyrin derivative having the formula A, in particular a derivative having the formula A1a described here above,
(ii) a compound having the formula I as defined here above,
(iii) a compound having the formula II as defined here above,
the said nanoparticles encapsulating gemcitabine or gemcitabine monophosphate.

A more particular embodiment of the invention relates to the nanoparticles, hereinafter referred to as "NPs CM240+ gemcitabine", formed by the elements constituted of:
(i) a porphyrin derivative having the formula A1a,
(ii) bis(triethoxysilyl)ethane,
(iii) bis triethoxysilylpropyl disulfide,
the said nanoparticles encapsulating gemcitabine.

An even more particular embodiment of the invention relates to nanoparticles, hereinafter referred to as "NPs CM240-b+gemcitabine", formed by the elements constituted of:
i) a porphyrin derivative having the formula A1a,
(ii) bis(triethoxysilyl)ethane,
(iii) bis triethoxysilylpropyl disulfide,
the molar proportion between porphyrin, bis(triethoxysilyl)ethane and bis triethoxysilylpropyl disulphide being, respectively, from 1% to 30% for the porphyrin derivative, from 40% to 90% for bis(triethoxysilyl)ethane, less than 50% for bis triethoxysilylpropyl disulfide,
the said nanoparticles encapsulating gemcitabine.

Another particular embodiment of the invention relates to the nanoparticles formed by the elements constituted of:
(i) a porphyrin derivative having the formula B,
(ii) a compound having the formula I as defined here above,
(iii) a compound having the formula II as defined here above,
the said nanoparticles encapsulating gemcitabine or gemcitabine monophosphate.

In a more particular embodiment of the invention, the nanoparticles, hereinafter referred to as "PMOS1+gemcitabine", formed by the elements constituted of:
(i) a porphyrin derivative having the formula B,
(ii) bis(triethoxysilyl)ethane
(iii) bis triethoxysilylpropyl disulfide
the said nanoparticles encapsulating gemcitabine.

The object of the present invention is also to provide a nanoparticle preparation method for preparing the nanoparticles as described here above.

The said method comprises the steps consisting of:
(a) reacting in an aqueous solution at a temperature of 20° C. to 50° C. in the presence of a surfactant, the compounds comprising:

(i) a porphyrin derivative selected from among:
a compound having the formula A
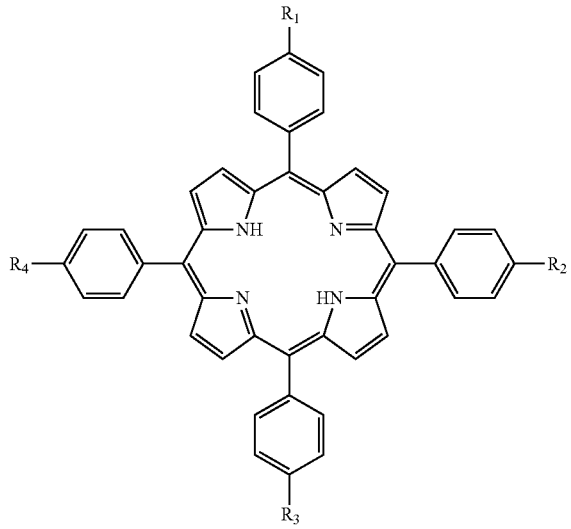
(A)
in which:
Either $R_1$, $R_2$, $R_3$, and $R_4$ all correspond to
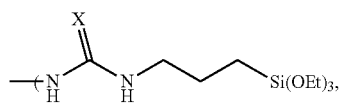
where X is the oxygen atom or the sulfur atom;
Or $R_1$, $R_2$, $R_3$, and $R_4$ all correspond to
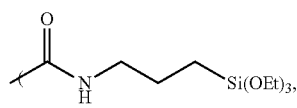
a compound having the formula B, C or D, in which Z is selected from the oxygen atom or the sulfur atom
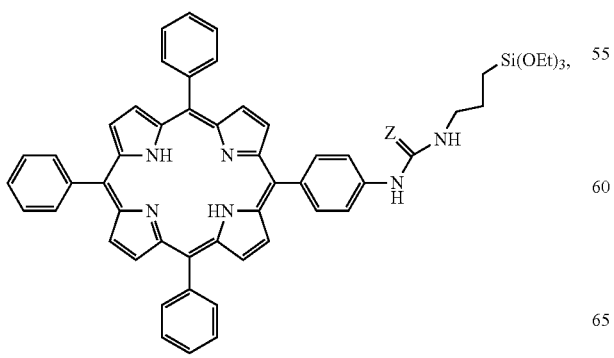
(B)
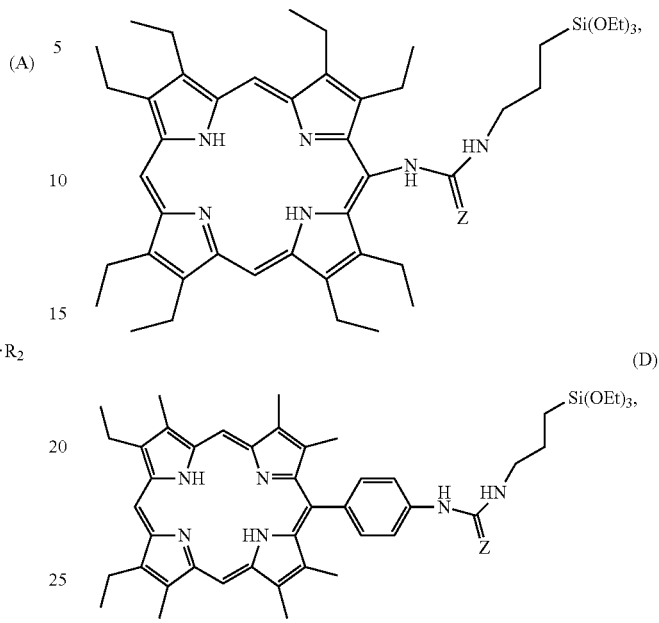
(C)
(D)
a compound E, F or G
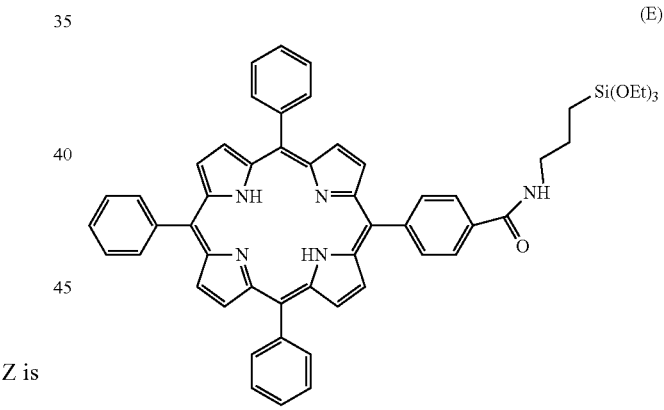
(E)
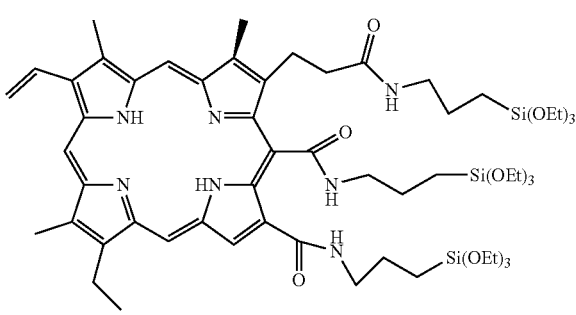
(F)

-continued (G)

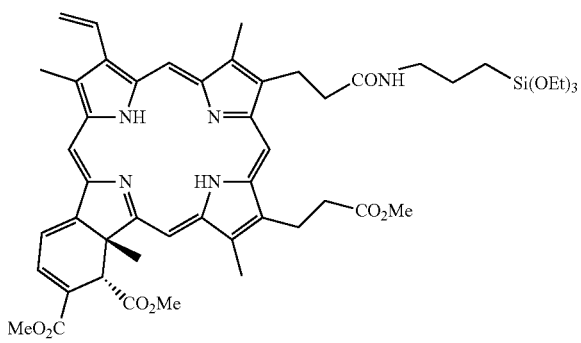

(ii) a compound having the formula I here below (EtO)$_3$Si(CH$_2$)$_n$Si(OEt)$_3$, in which n represents an integer selected from 1 to 10, and possibly (iii) a compound having the formula II (EtO)$_3$Si(CH$_2$)$_3$—(SS)$_m$—(CH$_2$)$_3$—Si(OEt)$_3$ in which m is an integer that is equal to 2 or 4, and (b) recovering the nanoparticles formed in the preceding step, and possibly, (c) reacting in a solvent, such as H$_2$O, Dimethyl Sulfoxide (DMSO), the nanoparticles obtained in the step (b) with at least one hydrophilic and/or hydrophobic anticancer compound in order to encapsulate the latter, (d) recovering the nanoparticles obtained at the end of the step (c).

The co-condensation between the porphyrin derivative as defined here above, the compound having the formula I and possibly the compound having the formula II forming the matrix of the nanoparticles of the invention, may be carried out in the presence of a surfactant in order to obtain the porosity of the system.

By way of example, the surfactant may be cetyttrimethylammonium bromide, cetyttrimethylammonium chloride, octadecyltrimethylammonium bromide, and cetyttrimethylammonium tosylate.

The step (a) of the method of the invention may be carried out in a basic aqueous solution, in particular at a pH of between 8 and 13.

The nanoparticles formed in the step (a) may be recovered by any techniques known to the person skilled in the art, in particular by centrifugation.

The implementation of the step (c) makes it possible to encapsulate at least one hydrophilic and/or hydrophobic anticancer compound in the pores of the nanoparticles recovered at the end of the step (b).

The invention also relates to the mesoporous organosilica nanoparticles obtained by the method of the invention.

The mesoporous organosilica nanoparticles of the invention may be used as a photosensitising agent for therapeutic or diagnostic purposes. These nanoparticles may be excited by one photon or two photons. Depending on the therapeutic objective and/or the type of condition or disease to be treated, it is possible to excite the nanoparticles of the invention with one photon or two photons in order to optimise the results desired. For example, in order to treat a relatively large surface area, it is advantageous to use one photon excitation, whereas excitation of the nanoparticles by two photons makes it possible to treat the tissues that are very localised.

The basic nanoparticles may be used alone for photodynamic therapy or as an encapsulating agent for the delivery of at least one hydrophilic and/or hydrophobic compound, in particular a hydrophilic compound.

The nanoparticles of the invention encapsulating at least one hydrophilic and/or hydrophobic anticancer compound may offer a synergy of anticancer activity related to both the properties of the anticancer compounds and the photosensitivity of the basic nanoparticles.

The mesoporous organosilica nanoparticles as described here above may be used as a medicament in the treatment of cancers, tumours, cell proliferative disorders and diseases, or skin conditions and diseases.

A medicinal product comprising the nanoparticles of the invention may be activated by infra-red radiation, which more effectively penetrates into the body than visible radiation, and may thus be used not only to treat superficial cancers, but also the cancerous tissues situated far deeper which cannot be accessed by the photosensitising agents known to date.

Among the various different cancers that the nanoparticles of the invention are capable of treating, mention may in particular be made of breast cancer, cervical cancer, colon cancer, epidermal cancer, lung cancer, ovarian cancer, prostate cancer, retinoblastoma as well as melanomas and all solid tumours that include, but are not limited to, neck and head cancers, digestive cancers, and all benign or cancerous tumours.

One object of the invention relates to pharmaceutical compositions comprising the nanoparticles as described here above and a pharmaceutically acceptable carrier.

The person skilled in the art will know how to select a suitable carrier based on their general knowledge according to the properties of the nanoparticles of the invention.

The nanoparticles of the invention may be administered locally or systemically. Local administration may be carried out in particular by means of injection of the composition of nanoparticles in the proximity of the tumour zone. In the case of superficial tumours, the nanoparticle compositions may be administered via the topical route, in an appropriate galenic or dosage form (solution, suspension, paste, patch). Administration via a general route may be effected intravenously, intramuscularly, subcutaneously, intraperitoneally or rectally. Such formulations and their mode of preparation are well known to the person skilled in the art. The determined dosage of the active composition of nanoparticles and/or that of encapsulated the anticancer compound is adapted according to the weight and age of the patient, the nature, the location and the stage of development of the tumour, the route of administration selected, and the dose of radiation used. Additionally, the composition may further comprise any other known active ingredient for the treatment of tumours and/or symptoms thereof. It comprises the conventional galenical components that are adapted to the chosen mode of administration. In particular, it may be in a galenic or dosage form that promotes vectorisation and targetting to the target tissues. For the treatment of internal tissues, once after parenteral administration of a pharmaceutical composition of the invention, a light source or laser may be introduced to the tissues to be treated by making use of endoscopy or optical fibre catheters.

The object of the invention also relates to a detection kit for the detection of a pathology selected from among cancers, tumours and cell proliferative disorders and diseases, the kit comprising:

the nanoparticles as described here above or a medicine composition comprising the same; and the means that provide for pulsed or non-pulsed blue to near IR laser irradiation.

By way of example, these means may in particular be a laser diode or a femtosecond pulsed laser that make it possible to emit a light having a wavelength of 400 nm to 1000 nm respectively.

Due to the fact that the nanoparticles of the invention are capable of emitting a visible light or fluorescence after mono-photon or bi-photon irradiation, these nanoparticles may also be used as a luminescent agent or fluorescent agent in the field of imaging for the detection or monitoring by imaging, in particular by means of two-photon microscopy, of cancers, tumours, cell proliferative disorders and diseases, or skin conditions and diseases.

In particular, the nanoparticles in which the porphyrin derivatives having the formula A are embedded may be excited by two photons and are therefore suitable for use in two-photon excitation microscopy.

The term "two-photon excitation microscopy" is understood to refer to two-photon excited confocal fluorescence microscopy, that makes it possible to provide a high resolution sample image in 3 dimensions.

The figures and examples following here below serve the purpose of illustrating the present invention in further details and are in no way intended to signify a limitation in respect of the possible scope of the present invention.

DESCRIPTION

Examples

Figure 1:
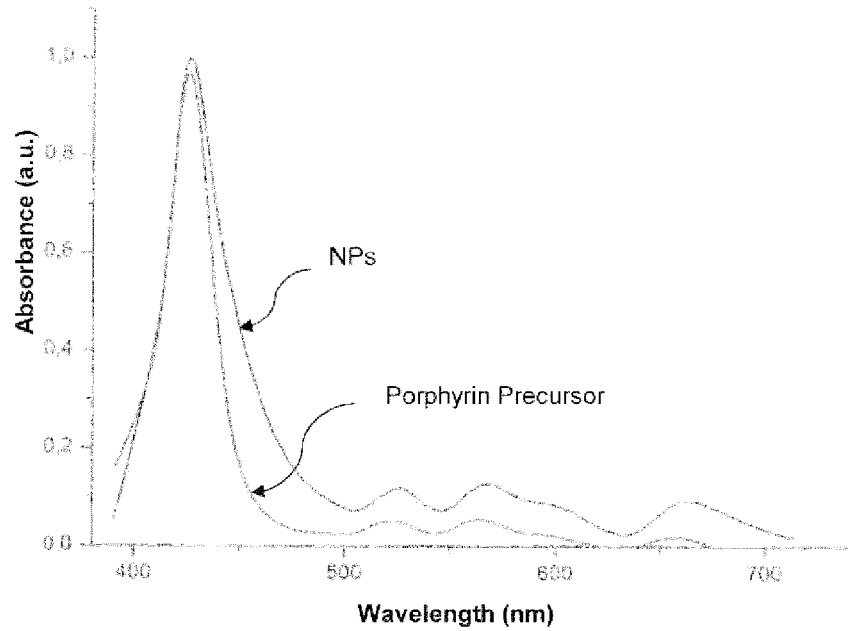
FIG. 1: Graph representing the UV-VIS spectrum of a solution of CM238 nanoparticles obtained after being put in suspension in ethanol.

1. Materials and Methods
1.1. Preparation of the CM238 Nanoparticles 250 mg of cetyitrimethylammonium bromide and 875 μL of NaOH (2M) are introduced into 120 mL of ultrapure water. The mixture is agitated at 750 revolutions per minute (rpm) for a period of 50 minutes at 80° C. The porphyrin having the formula A1a (in 1 ml of absolute ethanol) is introduced simultaneously in reaction with bis(triethoxysilyl)ethane (10/90 by weight). The reaction is maintained for a period of 1 hour 45 minutes at 80° C. Then the CM 238 nanoparticles obtained are centrifuged. The surfactant is extracted with an ethanolic solution of ammonium nitrate (6 g/L). The nanoparticles are put in suspension in this solution (50 ml) for a period of 30 minutes under ultrasound at 50° C., and centrifuged at 20000 rpm for a period of 20 minutes. The protocol is repeated three times. Three washes with ethanol are then carried out. The nanoparticles are dried under vacuum.

1.2 Preparation of the CM240 Nanoparticles

2M NaOH (875 µl) and the cetyitrimethylammonium bromide (250 mg) are mixed in 120 ml of water at 80° C. for a period of 120 minutes. The porphyrin having the formula A1a ($1.40 \times 10^{-2}$ mmol, 23.8 mg diluted in 1 mL of EtOH), bis(triethoxysilyl)ethane (1.78 mmol) and bis triethoxysilylpropyl disulfide (1.3 mmol) (ratio 1/55/44 in moles) are then added. The reaction is maintained for a period of 2 hours at 80° C., at 750 rpm. The nanoparticles are thereafter centrifuged at 20,000 rpm for a period of 15 minutes. The surfactant is extracted with an ethanoic solution of ammonium nitrate (6 g/L). The nanoparticles are put in suspension in this solution (50 ml) for a period of 30 minutes under ultrasound at 50° C., and centrifuged. The protocol is repeated three times. The nanoparticles are dried under vacuum.

1.3 Preparation of the CM240-b Nanoparticles

2M NaOH (875 µl) and the cetyitrimethylammonium bromide (250 mg) are mixed in 120 ml of water at 80° C. for a period of 120 minutes. The porphyrin having the formula A1a ($1.40 \times 10{-2}$ mmol, 23.8 mg diluted in 1 mL of EtOH), bis(triethoxysilyl)ethane (1.78 mmol) and bis triethoxysilylpropyl disulfide (0.3 mmol) (ratio 1/83/16 in moles) are then added. The reaction is maintained for a period of 2 hours at 80° C. at 750 rpm. The nanoparticles are thereafter centrifuged at 20,000 rpm for a period of 15 minutes. The surfactant is extracted with an ethanolic solution of ammonium nitrate (6 g/L). The nanoparticles are put in suspension in this solution (50 ml) for a period of 30 minutes under ultrasound at 50° C., and centrifuged. The protocol is repeated three times. The nanoparticles are dried under vacuum.

1.4. Preparation of the PMOS1 Nanoparticles

2M NaOH (437 µl) and cetyttrimethylammonium bromide (125 mg) are mixed in 60 ml of water at 80° C. for a period of 120 minutes. The porphyrin having the formula B ($1.3 \times 10 -2$ mmol, 12 mg diluted in 1 mL of EtOH) and bis(triethoxysilyl)ethane (0.89 mmol) are then added. The reaction is maintained for a period of 2 hours at 80° C. at 750 rpm. The nanoparticles are thereafter centrifuged at 20,000 rpm for a period of 15 minutes. The surfactant is extracted with an ethanoic solution of ammonium nitrate (6 g/L). The nanoparticles are put in suspension in this solution (50 ml) for a period of 30 minutes under ultrasound at 50° C., and centrifuged. The protocol is repeated three times. The nanoparticles are dried under vacuum.

1.5. Encapsulation of Gemcitabine 1.6 mg of CM238 nanoparticles are put in suspension with 1.9 mg of gemcitabine in 2 mL of water (pH=7.4) for a period of 24 hours. The nanoparticles are thereafter centrifuged and washed 4 times with water and dried under vacuum. The supernatants are collected in order to determine the quantity of medicament encapsulated in the nanoparticles.

1.6. UV-Vis Spectrum of the Nanoparticles 1 mg of nanoparticles are dispersed in 1 mL of EtOH. The UV-Vis spectrum of the nanoparticles is observed by using a UV-Vis spectrometer.

1.7. Two-Photon Confocal Microscopy Imaging of Cells

The MCF-7 breast cancer cells are incubated for a period of 20 hours with the nanoparticles. 15 minutes prior to imaging, the membranes of the cells are stained with a dye. The nanoparticles are observed at 750 nm with a two-photon confocal microscope and a low power laser (5% of the total power (3 W) delivered by the Chameleon femtosecond pulsed laser).

1.8. Release Kinetics of the Encapsulated Gemcitabine

The "NPs+gemcitabine" nanoparticles are introduced at the bottom of a UV tank and thereafter followed by addition of an aqueous solution at pH 7.4 without agitation. The concentration of gemcitabine released into the solution is measured after a period of 10, 20, 30 minutes. HCl is added into the solution after a period of 50 minutes. The concentration of gemcitabine released into the solution is then measured at 60, 90, 120, 130 and 140 minutes.

1.9. Cytotoxicity of the Nanoparticles

The MCF-7 cancer cells are incubated for a period of 20 hours with different concentrations of the nanoparticles. The cytotoxicity of the nanoparticles is measured without or after excitation. The excitation is carried out by means of Zeiss LSM 780 confocal microscope (×10 lens) at 800 nm.

The quantification of living cells is obtained by means of the MTT (3-(4, 5-dimethytthiazolyl-2)-2, 5-diphenytetrazolium bromide) assay (cell survival test) after 48 hours of irradiation. The MTT assay is carried out in accordance with a conventional protocol (Mosmann, *Journal of Immunological Methods*, 1983, 65 (1-2): 55-63).

1.10 Determination of ROS Production

The generation of ROS (Reactive Oxygen Species) is examined in cells by using the DCFDA (dichlorodihydrofluorescein diacetate) kit. In contact with ROS species, the non-fluorescent DCFDA is oxidised into fluorescent dihydrofluorescein (DCF).

Prior to the two-photon irradiation, the DCFDA was therefore incubated for a period of 45 minutes with the cells after endocytosis of the nanoparticles. The experiment reveals no significant fluorescence without irradiation while a high fluorescent signal is detected during the irradiation of the cells, which confirmed the production of ROS with two photon excitation (TPE). The intensity of the fluorescence is proportional to the quantity of ROS generated (detection at 535 nm).

2. Results 2.1. Analysis of the CM238 Nanoparticles

The CM 238 nanoparticles obtained have a very high specific surface area (832 $m^2$ $g^{-1}$) and a pore size of 3 nm. They are monodisperse with a diameter of 200-250 nm. They disperse in water or ethanol. The porphyrins in these nanoparticles aggregate into J aggregates with a shift of the UV-Vis spectrum towards red (red-shifted) (FIG. 1).

Figure 2:
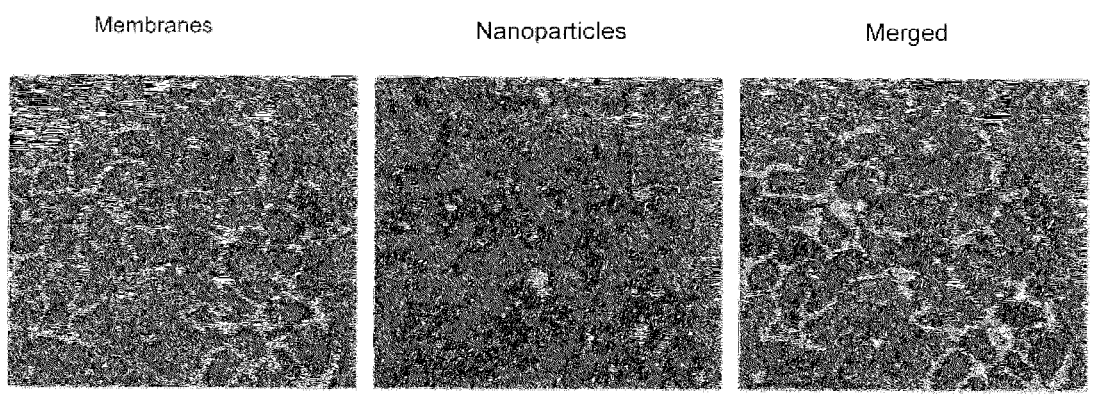
FIG. 2: Two-photon confocal microscopy imaging of MCF-7 cancer cells surviving after 20 hours of incubation with CM238 nanoparticles. At left: fluorescence of the membrane marker; in the middle: fluorescence emitted by the living cells at 750 nm; at right: superposition of the two images of fluorescence illustrated in the figures on the left and in the middle.

These particles may be used for the two-photon imaging of cancer cells. The MCF-7 breast cancer cells are incubated for a period of 20 hours with the CM238 nanoparticles and then observed at 750 nm with a confocal microscope and low power laser (5% of the total power (3 W) delivered by the Chameleon femtosecond pulsed laser). This experiment shows that the nanoparticles are internalised within the MCF-7 cells (FIG. 2).

Figure 3:
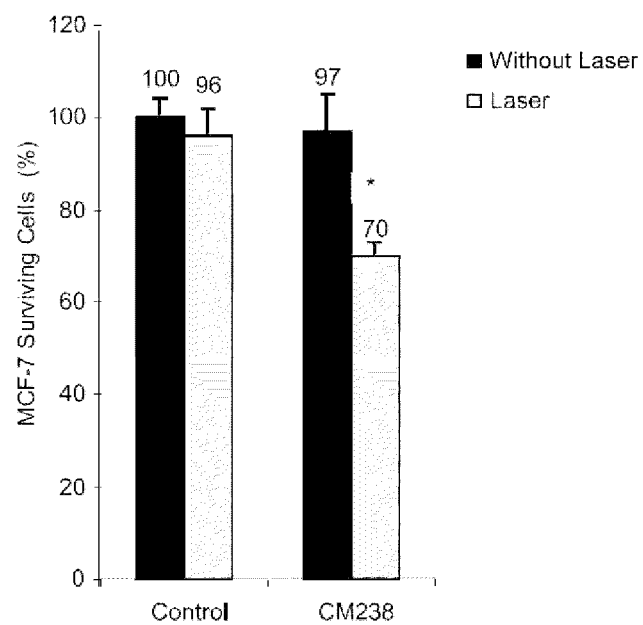
FIG. 3: Percentage of surviving MCF-7 cells before (black bar) and after (white bar) excitation at 800 nm by 3 scans of 1.57 s at maximum power by making use of a microscope and a two-photon laser, after 20 hours of incubation in a control culture medium ("Control") or with 80 μg/ml of CM238 nanoparticles.
Figure 11:
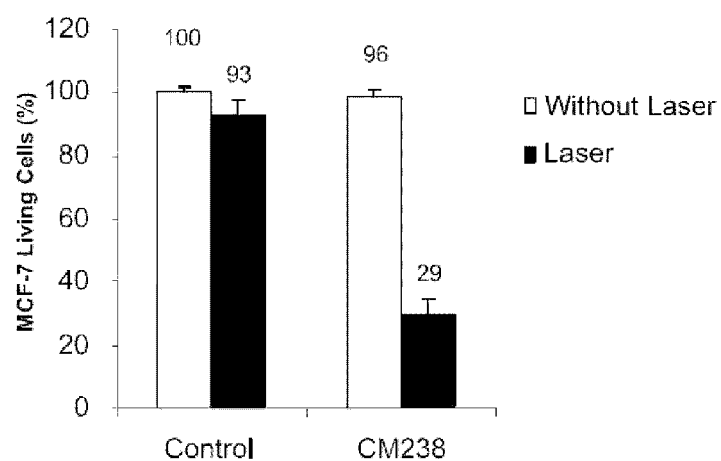
FIG. 11: Percentage of MCF-7 cells surviving before (white bar) and after (black bar) one-photon laser excitation with 10 mW power at 405 nm for a period of 10 min after 20 hours of incubation in a control culture medium ("Control") or with 80 μg/ml of CM238 nanoparticles.

After 20 hours of incubation of the MCF-7 cancer cells with 80 µg/ml of CM238 nanoparticles, the cells are irradiated with 3 scans of 1.57 s at 800 nm by two-photon confocal microscopy. About 27% of the cancer cells are destroyed after irradiation (FIG. 3). Under the same conditions of incubation, the cells are irradiated for a period of 10 minutes by means of a one-photon laser at 405 nm and a power measuring 10 mW. 71% of the cells are destroyed (FIG. 11).

Figure 12:
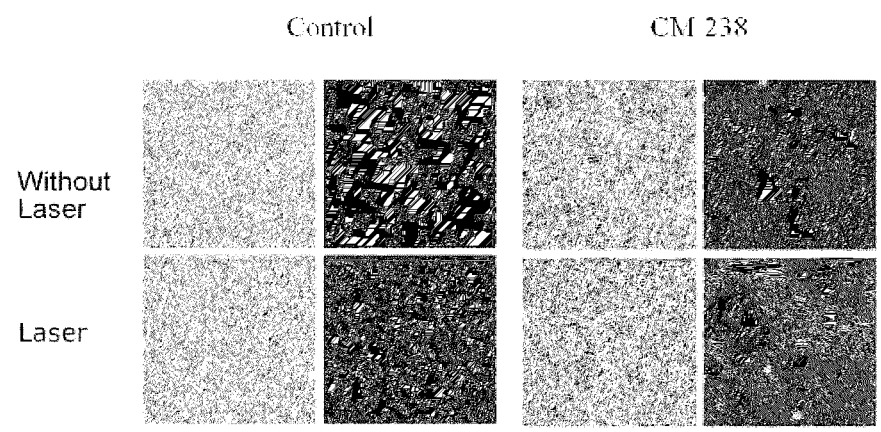
FIG. 12: Detection of ROS (Reactive Oxygen Species) from MCF-7 cells incubated for a period of 24 hours with 80 μg/ml of CM 238 nanoparticles.

The production of ROS is consistent with two-photon irradiation and is proportional to the intensity of fluorescence (FIG. 12).

2.2. Analysis of the "CM238+Gemcitabine" Nanoparticles

The CM238 basic nanoparticles, the matrix of which is formed by a porphyrin derivative having the formula A1a and bis(triethoxysilyl)ethane, are obtained according to the method described in section 1.1.

The gemcitabine is encapsulated within the CM238 nanoparticles according to the method described in section 1.2.

The gemcitabine load by weight relative to the weight of the basic nanoparticles is 50%. This signifies that gemcitabine is encapsulated effectively within the basic nanoparticles.

Figure 4:
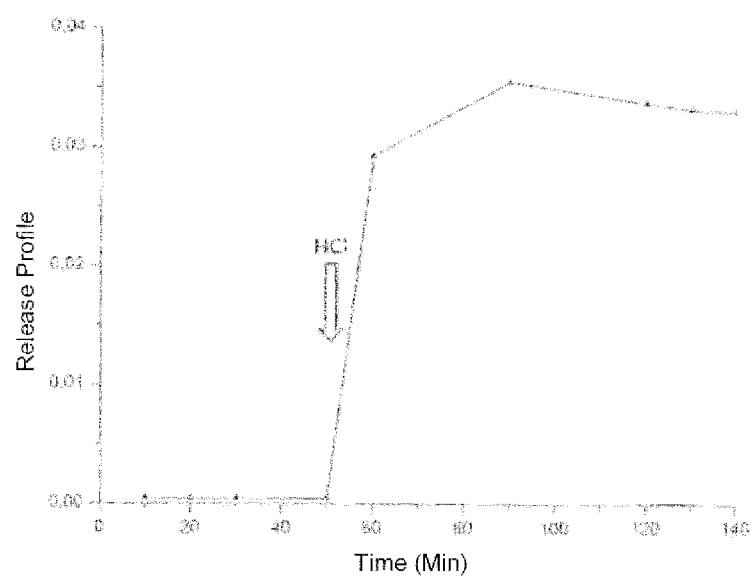
FIG. 4: Profile of the release, in water, of the encapsulated gemcitabine, from the "CM238+gemcitabine" Nanoparticles. The arrow signifies the addition of HCl. The abscissa or x-axis represents the time in minutes. The ordinate or y-axis represents the gemcitabine released.

The delivery of gemcitabine is sensitive to pH. At pH 7.4, the nanoparticles in suspension do not release gemcitabine, whereas at pH 5.5 (pH of the cancer cells), there is a significant delivery of gemcitabine (FIG. 4).

Figure 5:
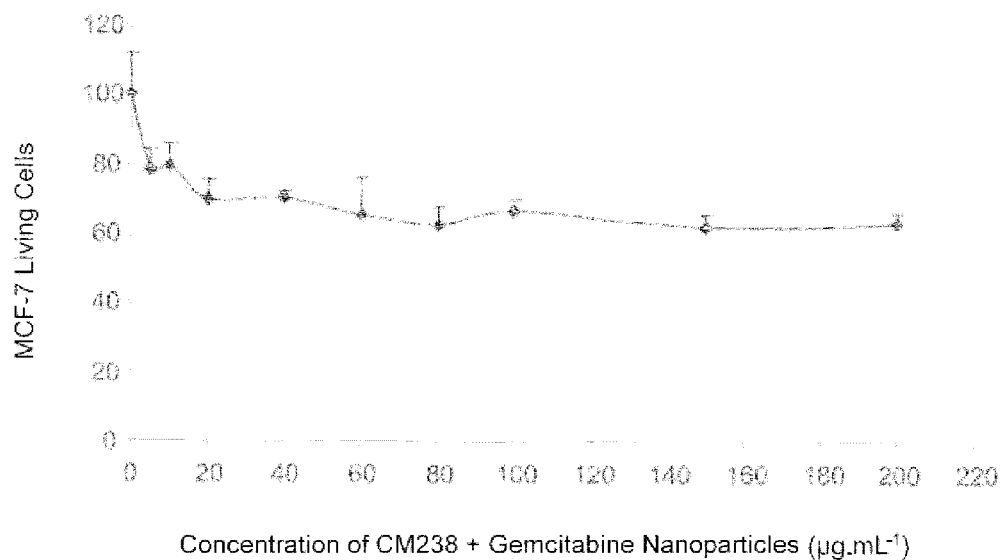
FIG. 5: Cytotoxicity of the "CM238+gemcitabine" nanoparticles on MCF-7 cells in the absence of excitation. The abscissa axis represents the concentration of nanoparticles expressed in μg/mL. The ordinate axis represents the percentage of surviving cells as determined by the MTT (3-(4, 5-dimethytthiazolyl-2)-2, 5-diphenytetrazolium bromide) assay.

The cytotoxicity of the "CM238+gemcitabine" nanoparticles at various different concentrations without excitation was tested on MCF-7 cell cultures. After three days of incubation, up to 40% of the cells are destroyed (FIG. 5). These results show that gemcitabine is delivered efficiently in cancer cells.

Figure 6:
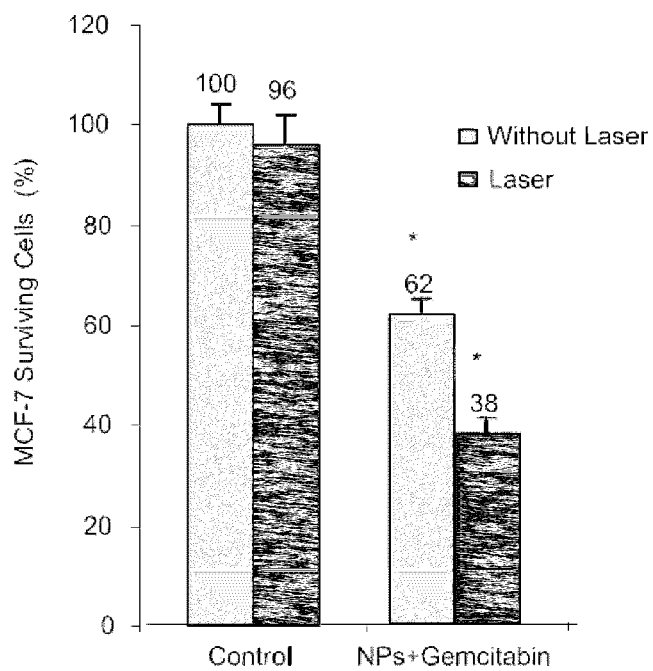
FIG. 6: Percentage of MCF-7 cells surviving before (light gray bar) and after (dark gray bar) excitation at 800 nm by 3 scans at maximum power by making use of two-photon microscopy, after 20 hours of incubation in a control culture medium ("Control") or with 40 μg/ml of "CM238+gemcitabine" nanoparticles.

When the "CM238+gemcitabine" nanoparticles are incubated at a concentration of 40 µg·mL$^{-1}$ for a period of 20 hours with the MCF-7 breast cancer cells, after irradiation at 800 nm with 3 scans at maximum power, 62% of the cells are destroyed due to dual treatment with gemcitabine and photodynamic therapy (FIG. 6).

2.3. Analysis of the CM240 Nanoparticles

Figure 7:
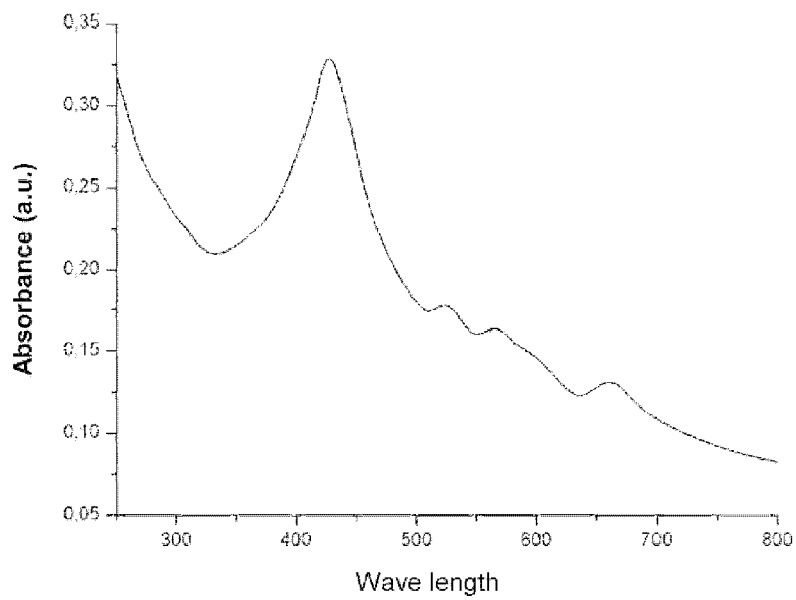
FIG. 7: Graph representing the UV-VIS spectrum of a solution of CM 240 nanoparticles obtained after its dispersion in ethanol.

The CM 240 nanoparticles obtained have a very high specific surface area (950 m$^2$ g$^{-1}$) and a pore size of 2.2 nm. They are monodisperse. They disperse in water or ethanol. The porphyrins in these nanoparticles aggregate into J aggregates with a shift of the UV-Vis spectrum towards red (red-shifted) (FIG. 7).

Figure 8:
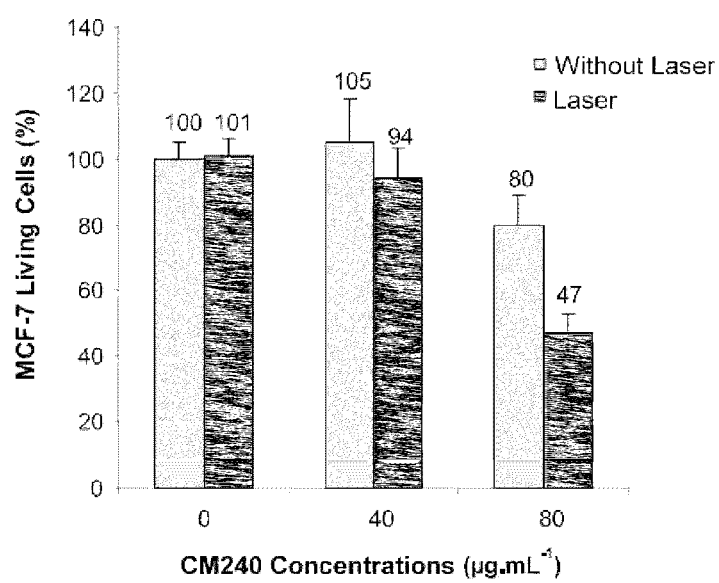
FIG. 8: Percentage of MCF-7 cells surviving before (light gray bar) and after excitation (dark gray bar) at 800 nm by 3 scans at maximum power using two-photon microscopy, after 20 hours of incubation in a control culture medium ("Control") or with 40 μg/ml or 80 μg/ml of CM240 nanoparticles.

At 80 µg/ml, after 20 hours of incubation with MCF-7 cancer cells, the CM240 nanoparticles after excitation at 800 nm by means of two-photon confocal microscopy using the Zeiss LSM 780 microscope (×10 lens), are able to destroy 53% of the cancer cells (FIG. 8). On the other hand, at 40 µg/ml, the CM240 nanoparticles do not show a significant cytotoxicity.

Figure 9:
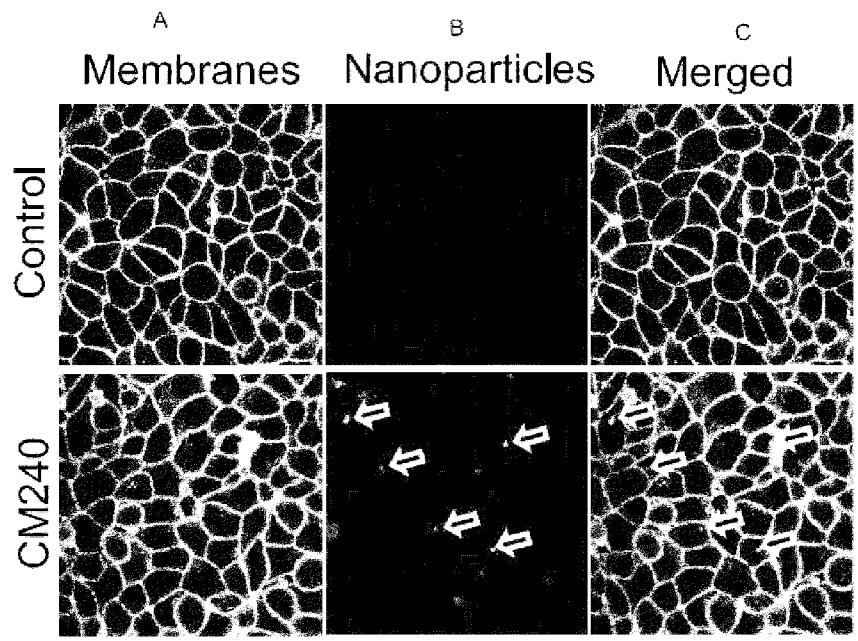
FIG. 9: Two-photon confocal microscopy imaging of surviving MCF-7 cancer cells after 20 hours of incubation in a control culture medium (top) or with 80 μg/ml of CM240 nanoparticles (bottom). Column A: fluorescence of the membrane marker; Column B: fluorescence emitted by the CM240 nanoparticles in the living cells at 800 nm; Column C: superposition of the two fluorescence images illustrated in the figures of columns A and B.

The surviving cells after 20 hours of incubation with 80 µg/ml of CM240 nanoparticles are observed by means of Zeiss LSM 780 two-photon confocal microscope (×63 lens). It is observed that the nanoparticles have entered into the cells (FIG. 9).

Figure 10:
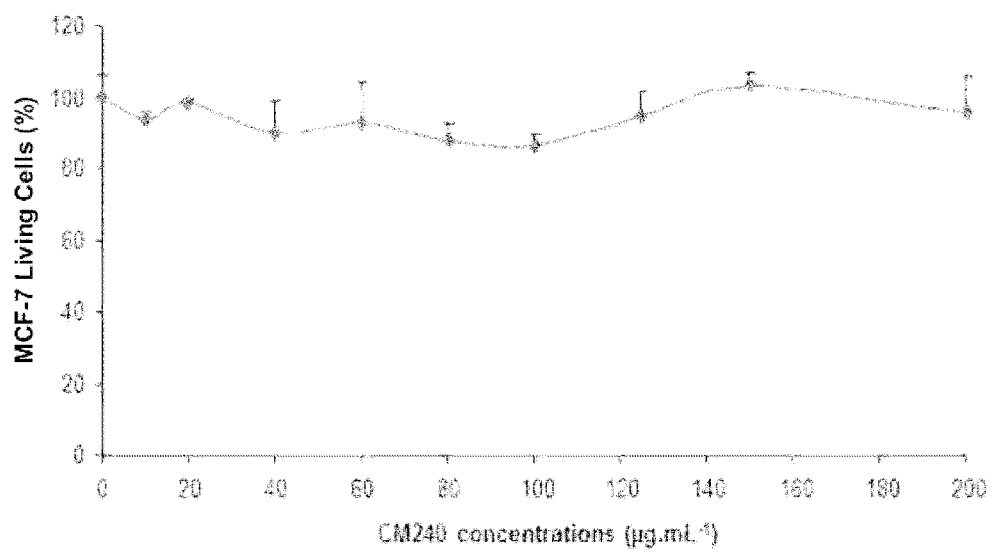
FIG. 10: Cytotoxicity of the CM240 nanoparticles on MCF-7 cells in the absence of excitation. The abscissa axis represents the concentration of nanoparticles expressed in μg/ml. The ordinate axis represents the percentage of surviving cells as determined by the MTT assay.

Furthermore, when MCF-7 cells are treated with increasing concentrations of CM240, in the absence of excitation, the CM240 nanoparticles are not toxic to the cells (FIG. 10).

Figure 13:
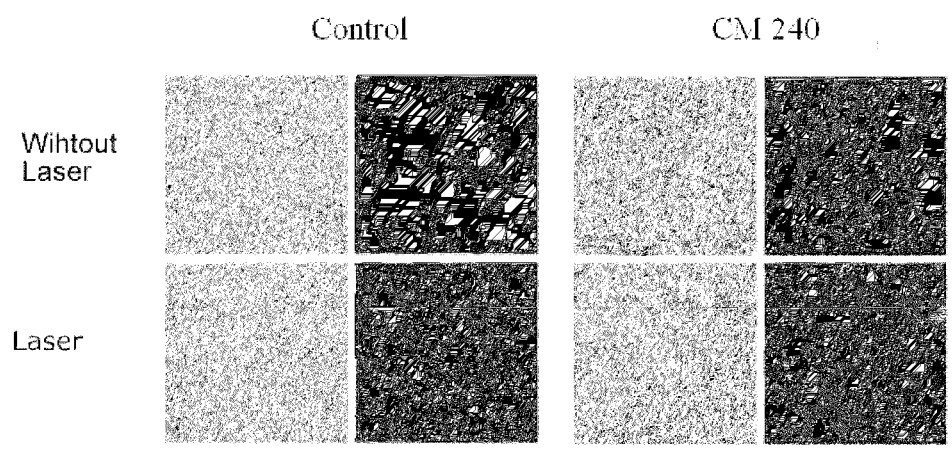
FIG. 13: Detection of ROS from MCF-7 cells incubated for a period of 24 hours with 80 μg/ml of CM 240 nanoparticles.

The production of ROS is consistent with two-photon irradiation and is proportional to the intensity of fluorescence (FIG. 13).

2.4. Analysis of the "CM240-b+Gemcitabine" Nanoparticles

The basic CM240-b nanoparticles whose matrix is formed by a porphyrin derivative having the formula A1a and bis(triethoxysilyl)ethane as well as bis triethoxysilylpropyl disulfide are obtained according to the method described in section 1.3.

The gemcitabine is encapsulated within the CM240-b nanoparticles according to the method described in section 1.5. The gemcitabine load by weight relative to the weight of the basic nanoparticles is 98%. This signifies that gemcitabine is encapsulated effectively within the basic nanoparticles.

Figure 14:
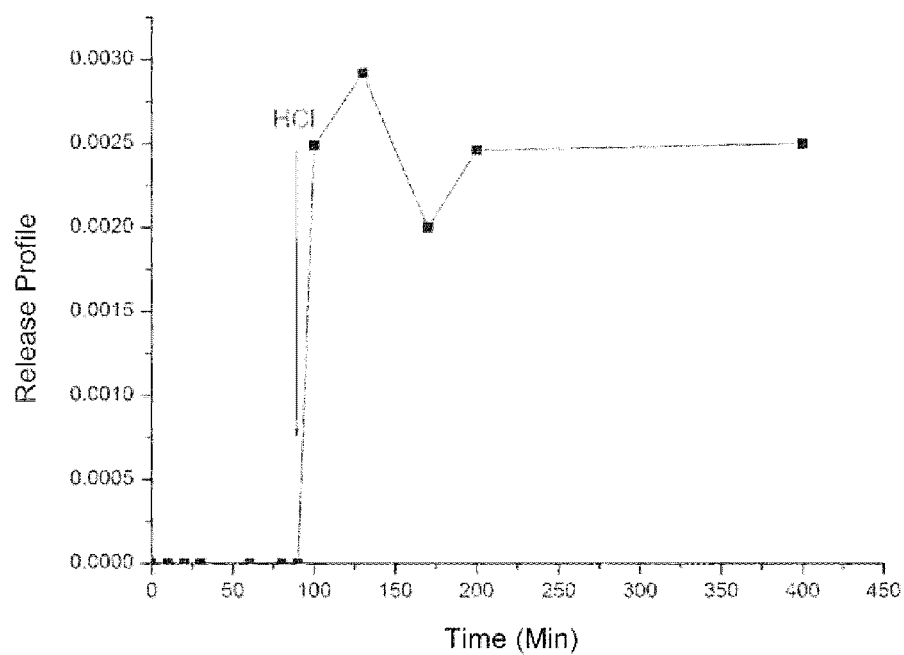
FIG. 14: Profile of the release, in water, of the encapsulated gemcitabine, from the "CM240-b+gemcitabine" nanoparticles. The arrow signifies the addition of HCl. The abscissa axis represents the time in minutes. The ordinate axis represents the gemcitabine released.

The delivery of gemcitabine is sensitive to pH. At pH 7.4, as well as at pH 5.5 (pH of the cancer cells), the nanoparticles in suspension do not release gemcitabine (FIG. 14).

2.5. Analysis of the PMOS1 Nanoparticles

The PMOS1 nanoparticles obtained have a very high specific surface area (892 m2 g-1) and a pore size of 3 nm. They are monodisperse with an average diameter of 305 nm. They disperse in water or ethanol.

Figure 15:
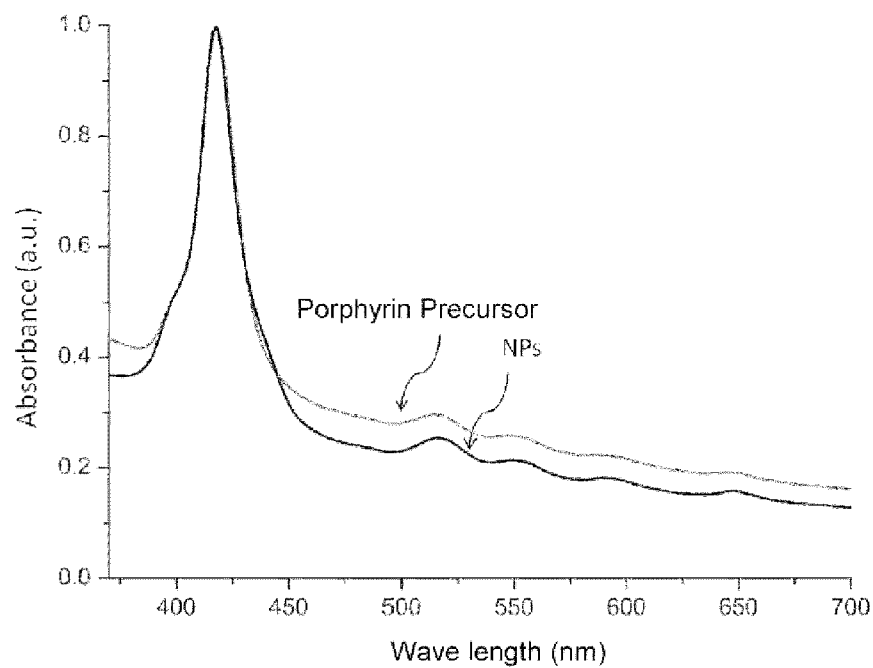
FIG. 15: Graph representing the UV-VIS spectrum of a solution of PMOS1 nanoparticles obtained after being put in suspension in ethanol.

The porphyrins in these nanoparticles show no shift in the UV-Vis spectrum as compared to the porphyrin derivative thereof having the formula B (FIG. 15). These particles may thus be used for one-photon imaging of cancer cells. The MCF-7 breast cancer cells are incubated for a period of 20 hours with the PMOS1 nanoparticles and then observed at 850 nm.

Figure 16:
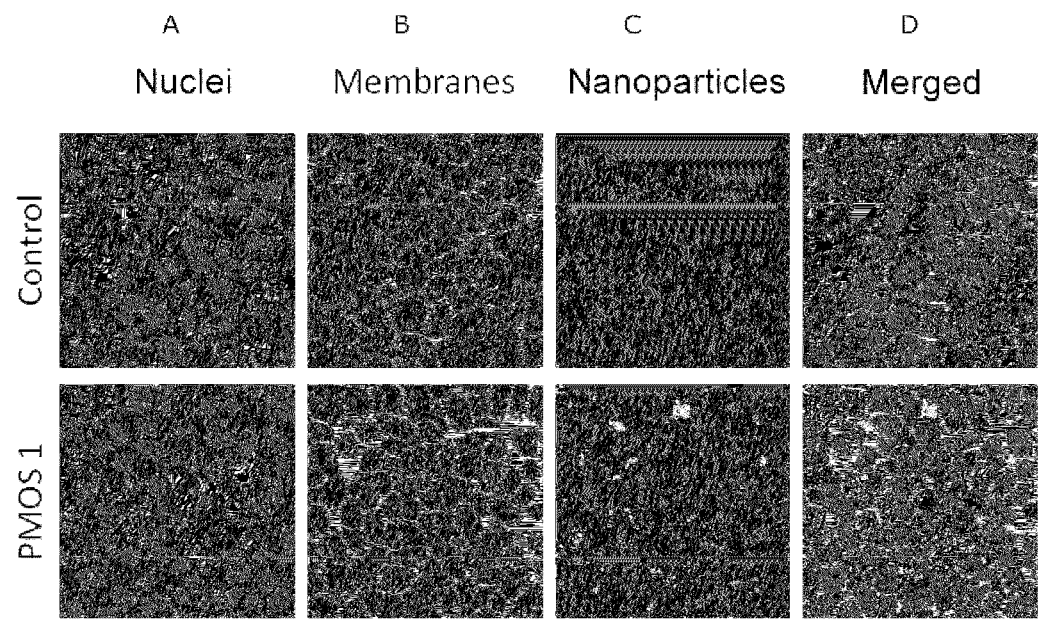
FIG. 16: Two-photon confocal microscopy imaging of MCF-7 cancer cells surviving after 20 hours of incubation in a control culture medium (top) or with 80 μg/ml of PMOS1 nanoparticles (bottom). Column A: fluorescence of the nuclei; Column B: fluorescence of the membrane marker; Column C: fluorescence emitted by the PMOS1 nanoparticles in the living cells at 850 nm; Column D: superposition of the two fluorescence images illustrated in the figures of columns A, B and C.

This experiment shows that the nanoparticles are internalised within the MCF-7 cells (FIG. 16).

Figure 17:
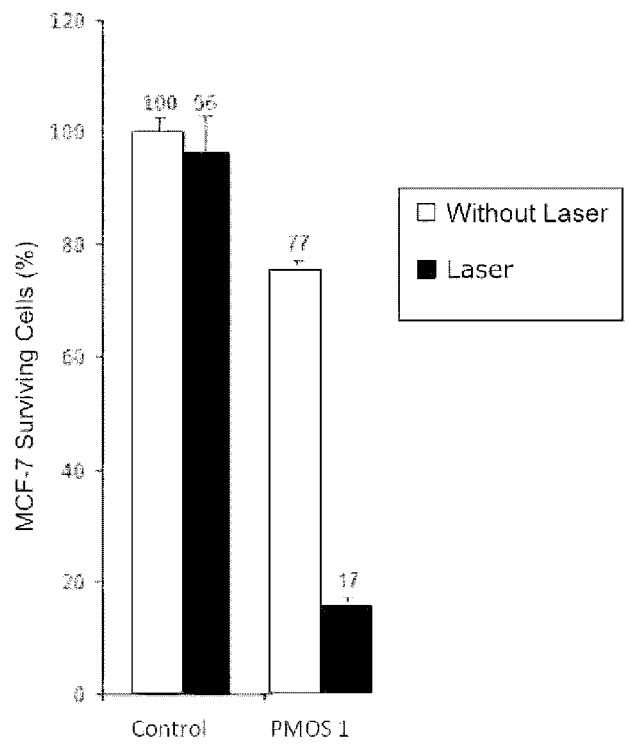
FIG. 17: Percentage of MCF-7 cells surviving before (white bar) and after (black bar) one-photon laser excitation with 10 mW power at 405 nm for a period of 10 min after 20 hours of incubation in a control culture medium ("Control") or with 80 μg/ml of PMOS1 nanoparticles.

After 20 hours of incubation of the MCF-7 cancer cells with 80 µg/ml of PMOS1 nanoparticles, the cells are irradiated at 405 nm by means of a one-photon laser with a power measuring 10 mW. About 80% of the cancer cells are destroyed after irradiation (FIG. 17).

2.6. Analysis of the "PMOs1+Gemcitabine" Nanoparticles

The PMOS1 basic nanoparticles whose matrix is formed by a porphyrin derivative having the formula B and bis (triethoxysilyl)ethane are obtained according to the method described in section 1.4.

The gemcitabine is encapsulated within the PMOS1 nanoparticles according to the method described in section 1.5. The gemcitabine load by weight relative to the weight of the basic nanoparticles is 72%. This signifies that gemcitabine is encapsulated effectively within the basic nanoparticles.

Figure 18:
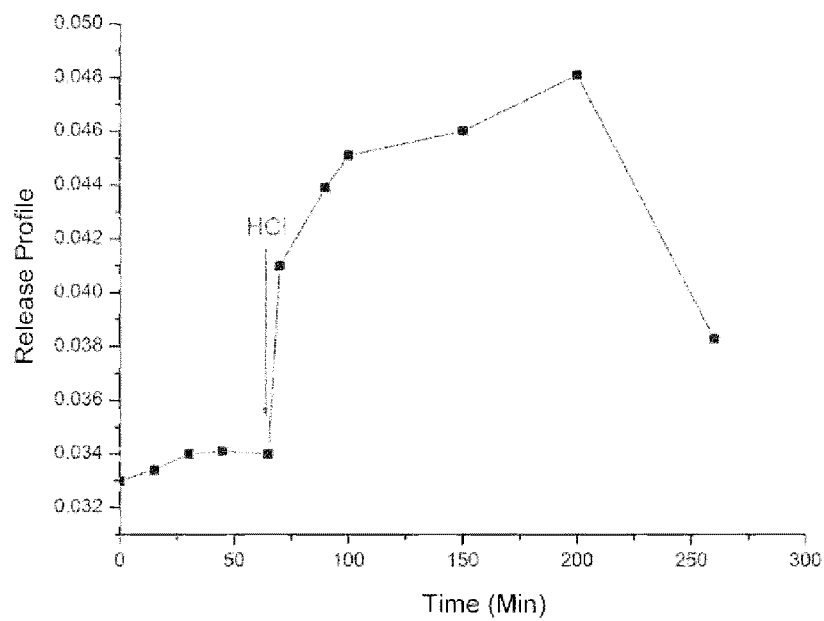
FIG. 18: Profile of the release, in water, of the encapsulated gemcitabine, from the "PMOS1+gemcitabine" nanoparticles. The arrow signifies the addition of HCl. The abscissa axis represents the time in minutes. The ordinate axis represents the gemcitabine released.

The delivery of gemcitabine is sensitive to pH. At pH 7.4, the nanoparticles in suspension do not release gemcitabine, and for the most part not even at pH 5.5 (pH of the cancer cells), where only 0.5% is released (FIG. 18).

The invention claimed is:

1. Mesoporous organosilica nanoparticles comprising:
   (i) a porphyrin derivative being a compound having the formula A

23

(A)

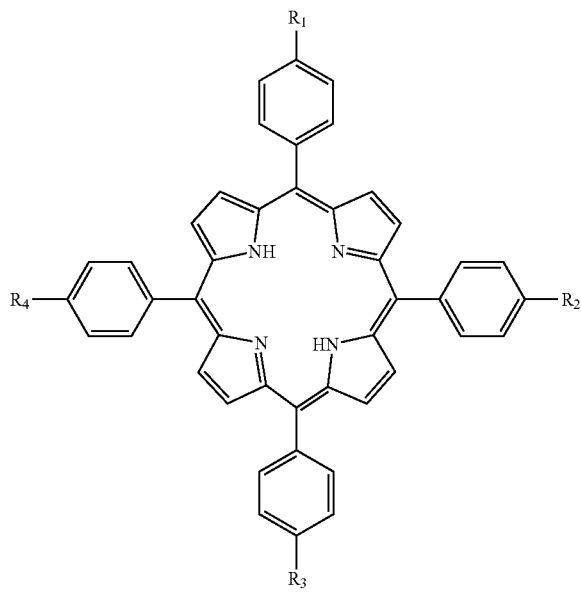

in which:
either $R_1$, $R_2$, $R_3$, and $R_4$ all correspond to

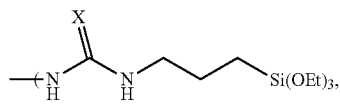

where X is an oxygen atom or a sulfur atom;
or $R_1$, $R_2$, $R_3$, and $R_4$ all correspond to

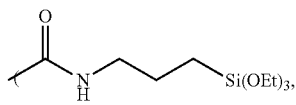

(ii) a compound having the formula I:

in which n represents an integer selected from 1 to 10, wherein the porphyrin derivative aggregates into a J aggregate and wherein the nanoparticles optionally encapsulate at least one hydrophilic and/or hydrophobic anticancer compound.

2. The nanoparticles according to claim 1, wherein the hydrophilic anticancer compound is selected from the group consisting of gemcitabine, gemcitabine monophosphate, 5-fluorouracil, cytarabine, topotecane, irinotecane, and oxalylplatin; wherein the hydrophobic anticancer compound is selected from the group consisting of doxorubicin, paclitaxel, and camptothecin.

3. The nanoparticles according to claim 1, formed by the elements comprising:
(i) a porphyrin derivative having the formula here below:

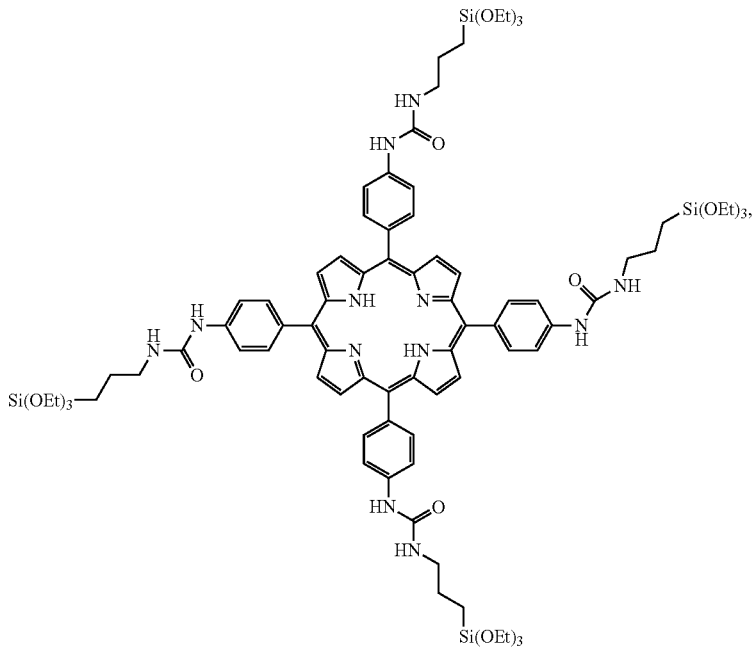

and
(ii) a compound of formula I, as defined according to claim 1.

4. The nanoparticles according to claim 1, comprising:
(i) a porphyrin derivative having the formula here below:

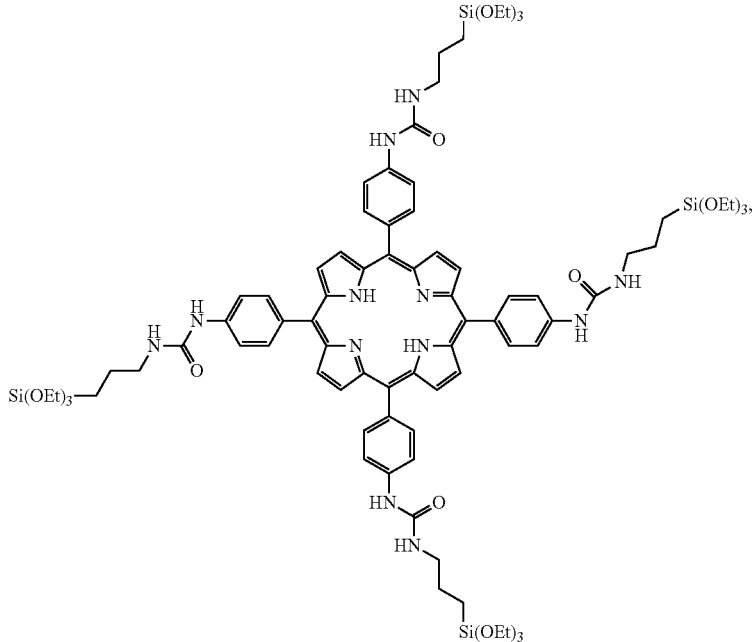

and
(ii) a compound having the formula I as defined in claim 1,
wherein the nanoparticles encapsulate gemcitabine or gemcitabine monophosphate.

5. The nanoparticles according to claim 1, comprising:
(i) a porphyrin derivative having the formula here below:

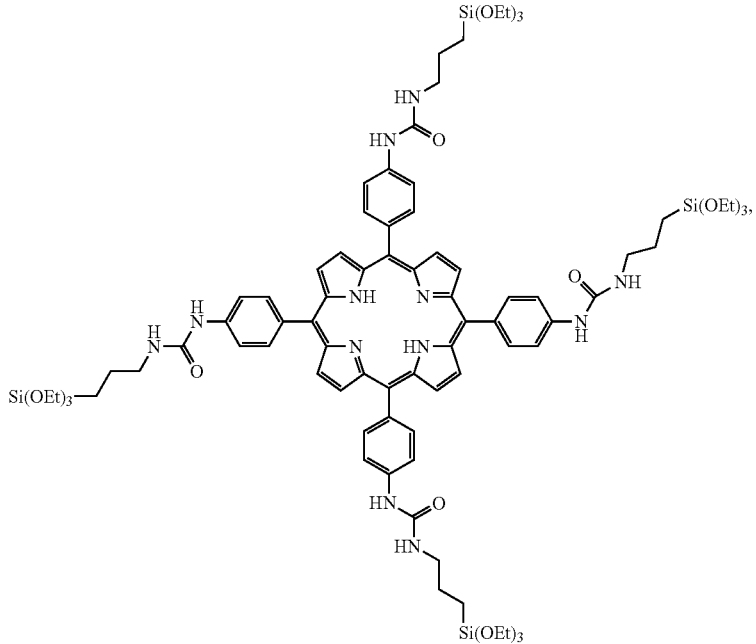

(ii) a compound having the formula I as defined according to claim 1, and
(iii) a compound having the formula II

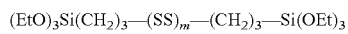

in which m is an integer that is equal to 2 or 4.

6. The nanoparticles according to claim 1, comprising:
(i) a porphyrin derivative having the formula:

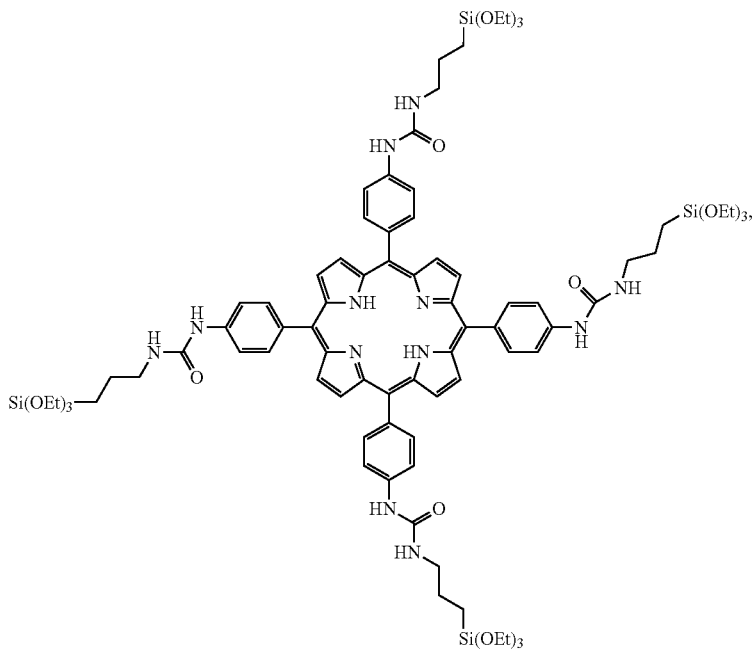

(ii) a compound having the formula I as defined according to claim 1, and
(iii) a compound having the formula II

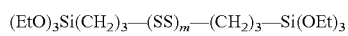

in which m is an integer that is equal to 2 or 4,
wherein the nanoparticles encapsulate gemcitabine or gemcitabine monophosphate.

7. The nanoparticles according to claim 1, wherein the molar ratio between the porphyrin derivative and the compound having the formula I is between 2:98 and 20:80.

8. The nanoparticles according to claim 1, wherein the load of hydrophilic or hydrophobic anticancer compound as defined in claim 1 is from 2% to 100% by weight relative to the initial weight of the nanoparticles prior to the encapsulation of the said anticancer compound.

9. The nanoparticles according to claim 1, whereof the diameter of particles is from 20 to 400 nm and the specific area is from 100 to 1500 m$^2$/g.

10. A method of treating cancers, tumors, cell proliferative disorders and diseases, or skin conditions and diseases comprising administering to a subject the nanoparticles according to claim 1.

11. A method of detecting or monitoring a cancer, a tumor, a cell proliferative disorder, a cell proliferative disease, a skin condition or a skin disease in a subject comprising:

administering to the subject the nanoparticles according to claim 1 as a luminescent agent or a fluorescent agent;

irradiating the nanoparticles with mono-photon or bi-photon irradiation; and detecting visible light or fluorescence emitted from the nanoparticles in order to detect or monitor the cancer, tumor, cell proliferative disorder, cell proliferative disease, skin condition or skin disease in the subject.

12. A method of photosensitizing a cell comprising administering to the cell the nanoparticles according to claim 1 as a photosensitizing agent.

13. A pharmaceutical composition comprising the nanoparticles as claimed in claim 1 and a pharmaceutically acceptable carrier.

14. A nanoparticle preparation method for preparing the nanoparticles according to claim 1, the said method comprises the steps of:

(a) reacting in a basic aqueous solution at a temperature of 50° C. to 90° C. in the presence of a surfactant, the compounds comprising:

(i) a porphyrin being a compound having the formula A

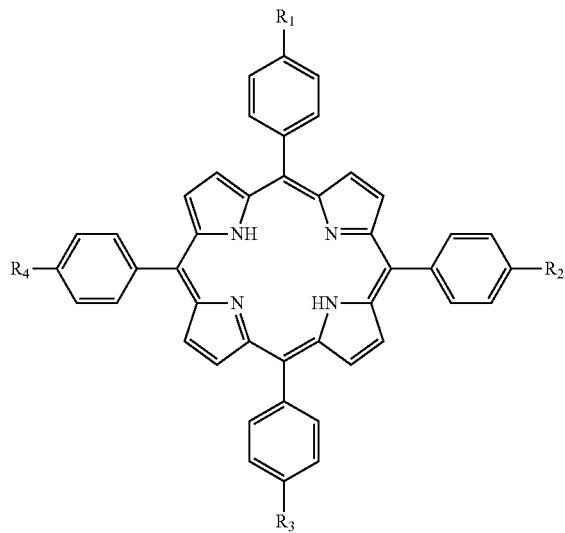

in which:
either $R_1$, $R_2$, $R_3$, and $R_4$ all correspond to

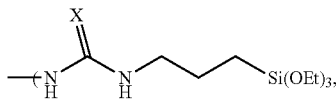

where X is an oxygen atom or a sulfur atom;
or $R_1$, $R_2$, $R_3$, and $R_4$ all correspond to

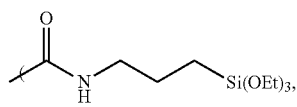

(ii) a compound having the formula I here below:

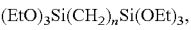

in which n represents an integer selected from 1 to 10, and (iii) optionally a compound having the formula II

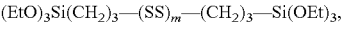

in which m is an integer that is equal to 2 or 4, and
(b) recovering the nanoparticles formed in the preceding step, and optionally: (c) reacting in a solvent, the nanoparticles obtained in the step (b) with at least one hydrophilic and/or hydrophobic anticancer compound in order to encapsulate the latter, and
(d) recovering the nanoparticles obtained at the end of the step (c).

15. Mesoporous nanoparticles obtained by the method according to claim 14.

16. A detection kit for the detection of a pathology selected from the group consisting of cancers, tumors and cell proliferative disorders and diseases, the kit comprising:
the nanoparticles according to claim 1 or a medicine composition comprising the same; and
a light source configured to provide LED, blue to near IR laser irradiation.

17. The nanoparticles according to claim 1, further comprising:
(iii) a compound having the formula II

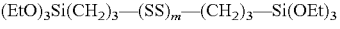

in which m is an integer that is equal to 2 or 4.

* * * * *